United States Patent
Lampropoulos et al.

(10) Patent No.: US 9,192,739 B2
(45) Date of Patent: Nov. 24, 2015

(54) ADJUSTABLE LENGTH CATHETER AND METHOD OF USE

(71) Applicant: Merit Medical Systems, Inc., South Jordan, UT (US)

(72) Inventors: Fred Lampropoulos, Salt Lake City, UT (US); Jim Mottola, West Jordan, UT (US); Brian Stevens, Pleasant Grove, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 14/041,833

(22) Filed: Sep. 30, 2013

(65) Prior Publication Data

US 2014/0094773 A1     Apr. 3, 2014

Related U.S. Application Data

(60) Provisional application No. 61/708,439, filed on Oct. 1, 2012.

(51) Int. Cl.
*A61M 25/00* (2006.01)
*B26D 3/16* (2006.01)

(52) U.S. Cl.
CPC ....... *A61M 25/0015* (2013.01); *A61M 25/0009* (2013.01); *A61M 25/0097* (2013.01); *B26D 3/166* (2013.01); *B26D 3/169* (2013.01)

(58) Field of Classification Search
CPC ............... A61M 25/0009; A61M 25/0015; A61M 25/00971; A61M 25/00; A61M 25/0014; A61M 25/002; A61M 25/0021; A61M 2025/0024; A61M 25/0043; A61M 25/0097; A61M 2025/0098; A61M 25/1025; A61M 25/1027; B26D 3/16; B26D 3/162; B26D 3/166; B26D 3/169
USPC .......................................................... 604/910
See application file for complete search history.

(56) References Cited

U.S. PATENT DOCUMENTS

| | | | | |
|---|---|---|---|---|
| 2,242,831 A | * | 5/1941 | Mcintosh | 72/317 |
| 2,876,496 A | * | 3/1959 | Murphy, Jr. | 264/294 |
| 3,094,124 A | * | 6/1963 | Birtwell | 604/523 |
| 4,068,515 A | * | 1/1978 | Kowal et al. | 72/115 |
| 4,256,106 A | * | 3/1981 | Shoor | 604/411 |
| 4,264,294 A | * | 4/1981 | Ruiz | 425/466 |
| 4,402,136 A | * | 9/1983 | Rast | 30/101 |

(Continued)

FOREIGN PATENT DOCUMENTS

| EP | 0109657 | 5/1984 |
|---|---|---|
| EP | 2392437 A1 * | 12/2011 |

OTHER PUBLICATIONS

International Search Report and Written Opinion dated Dec. 19, 2013 for PCT/US2013/062685.

*Primary Examiner* — Kevin C Sirmons
*Assistant Examiner* — William Carpenter
(74) *Attorney, Agent, or Firm* — Stoel Rives LLP

(57) ABSTRACT

An adjustable length catheter is disclosed. In some embodiments, the catheter is configured for use with a hub configured to couple to an end of the catheter. A cutting tool and/or a flaring tool may further be provided in connection with the catheter. In some embodiments, these tools are coupled to a body member. The catheter may be configured such that a user, for example a medical practitioner, may cut the catheter to a desired size as part of a therapy or other procedure.

16 Claims, 11 Drawing Sheets

(56) References Cited

U.S. PATENT DOCUMENTS

| | | | |
|---|---|---|---|
| 4,430,081 A * | 2/1984 | Timmermans | 604/256 |
| 4,535,616 A * | 8/1985 | Eason | 72/116 |
| 4,625,464 A * | 12/1986 | Kubo | 451/441 |
| 4,813,260 A * | 3/1989 | Strybel | 72/316 |
| 4,837,931 A * | 6/1989 | Beermann | 30/92 |
| 5,020,221 A * | 6/1991 | Nelson | 30/169 |
| 5,267,966 A * | 12/1993 | Paul | 604/167.04 |
| 5,283,951 A * | 2/1994 | Davenport et al. | 29/890.144 |
| 5,380,304 A * | 1/1995 | Parker | 604/526 |
| D372,782 S * | 8/1996 | Spehalski | D24/133 |
| 5,645,539 A | 7/1997 | Solomon et al. | |
| 6,994,009 B2 * | 2/2006 | Carter | 83/639.1 |
| 7,182,746 B2 | 2/2007 | Haarala et al. | |
| 7,318,334 B2 * | 1/2008 | Carter | 72/317 |
| 7,641,630 B2 | 1/2010 | Accisano, III et al. | |
| 7,740,616 B2 * | 6/2010 | Smith et al. | 604/174 |
| 7,938,809 B2 | 5/2011 | Lampropoulos et al. | |
| 8,177,771 B2 * | 5/2012 | Butts et al. | 604/523 |
| 2003/0217624 A1 * | 11/2003 | Dittmar | 83/13 |
| 2004/0040796 A1 | 3/2004 | Pham | |
| 2004/0171997 A1 * | 9/2004 | Wilson et al. | 604/284 |
| 2005/0182435 A1 * | 8/2005 | Andrews et al. | 606/172 |
| 2005/0192537 A1 * | 9/2005 | Osborne et al. | 604/167.01 |
| 2006/0137973 A1 * | 6/2006 | Herrington | 204/196.06 |
| 2006/0167417 A1 * | 7/2006 | Kratz et al. | 604/164.05 |
| 2006/0276773 A1 * | 12/2006 | Wilson et al. | 604/523 |
| 2007/0016167 A1 * | 1/2007 | Smith et al. | 604/533 |
| 2007/0175048 A1 * | 8/2007 | Holley et al. | 30/278 |
| 2008/0236358 A1 * | 10/2008 | Vitullo et al. | 83/663 |
| 2009/0158597 A1 * | 6/2009 | Braga et al. | 30/92.5 |
| 2009/0326560 A1 | 12/2009 | Lampropoulos et al. | |
| 2010/0031793 A1 * | 2/2010 | Hayner et al. | 83/54 |
| 2010/0331823 A1 * | 12/2010 | Blanchard | 604/533 |
| 2012/0253295 A1 * | 10/2012 | Nentwick et al. | 604/264 |

* cited by examiner

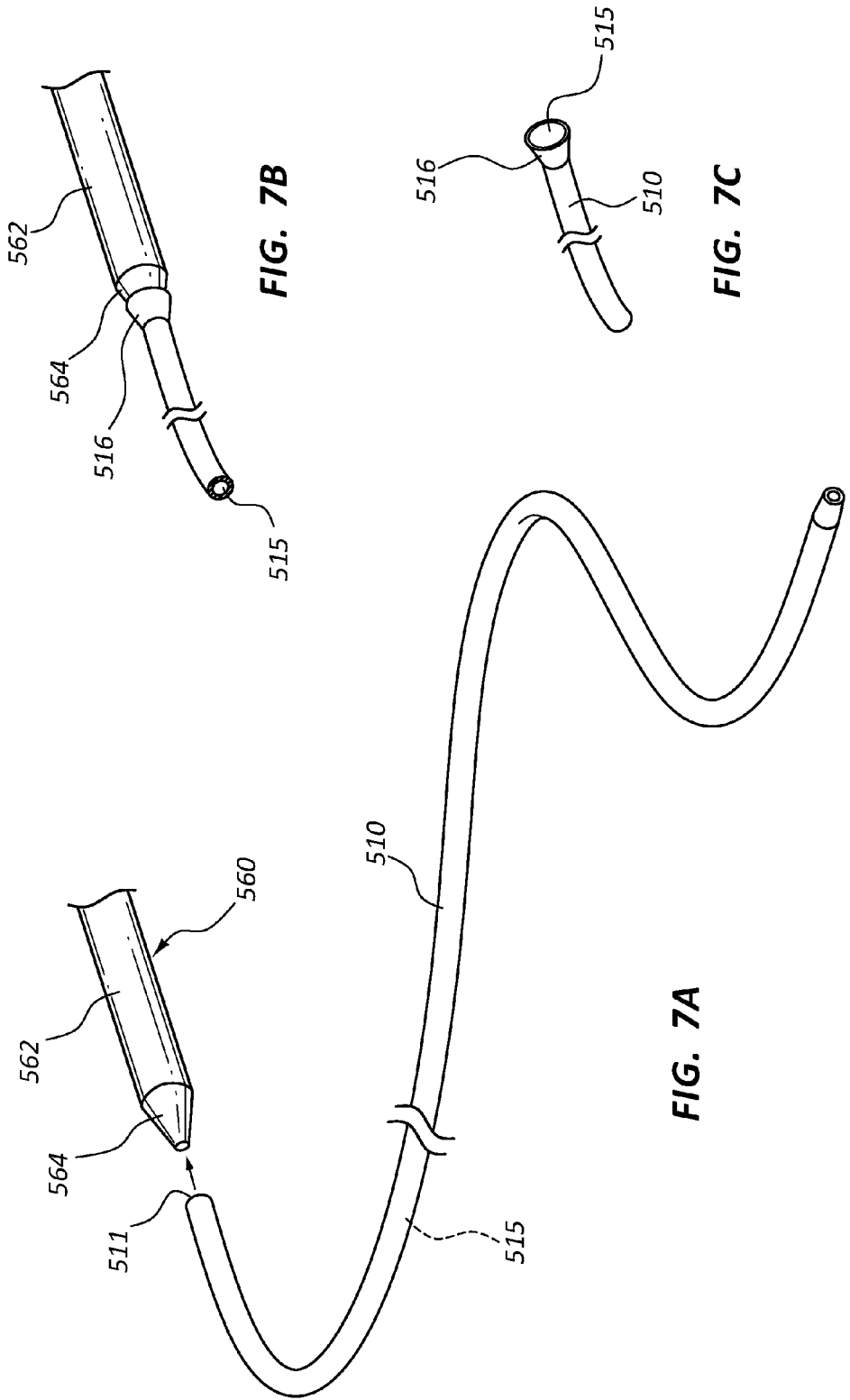

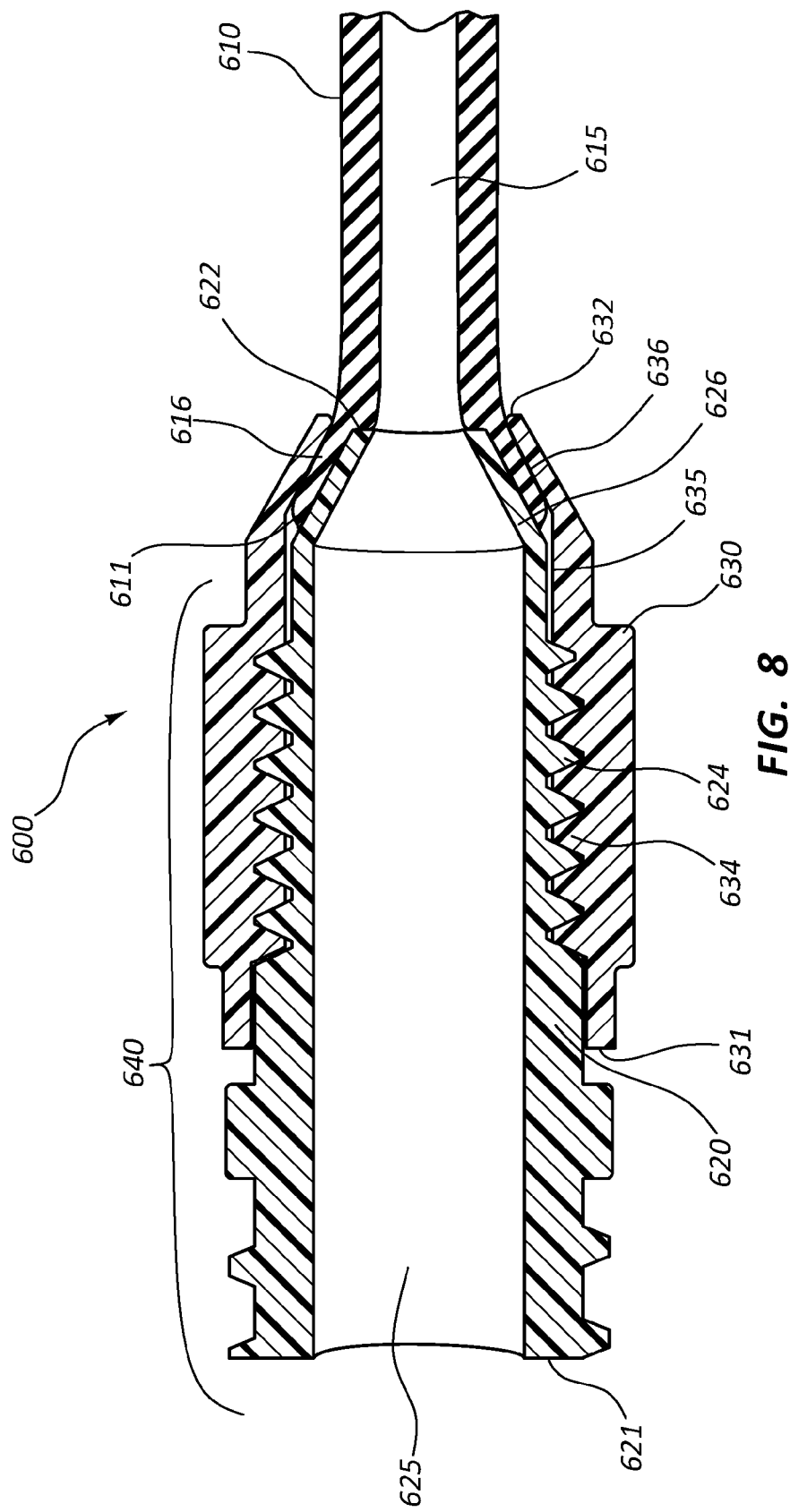

ADJUSTABLE LENGTH CATHETER AND METHOD OF USE

RELATED APPLICATION

This application claims priority to U.S. Provisional Application No. 61/708,439 filed on Oct. 1, 2012 and titled "Adjustable Length Catheter and Method of Use," the entirety of which is hereby incorporated by reference.

TECHNICAL FIELD

The present disclosure relates generally to elongate medical devices such as catheters. More specifically, the present disclosure relates to catheters that may be configured to be cut to a desired length by a user, such as a medical practitioner.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 7A is a perspective view of a catheter and an embodiment of a flaring tool in a first configuration.

FIG. 7B is a perspective view of the catheter and flaring tool of FIG. 7A in a second configuration.

FIG. 7C is a perspective view of the catheter of FIG. 7A in a third configuration.

FIG. 8 is a cross-sectional view of an embodiment of a catheter assembly.

DETAILED DESCRIPTION

Figure 1:
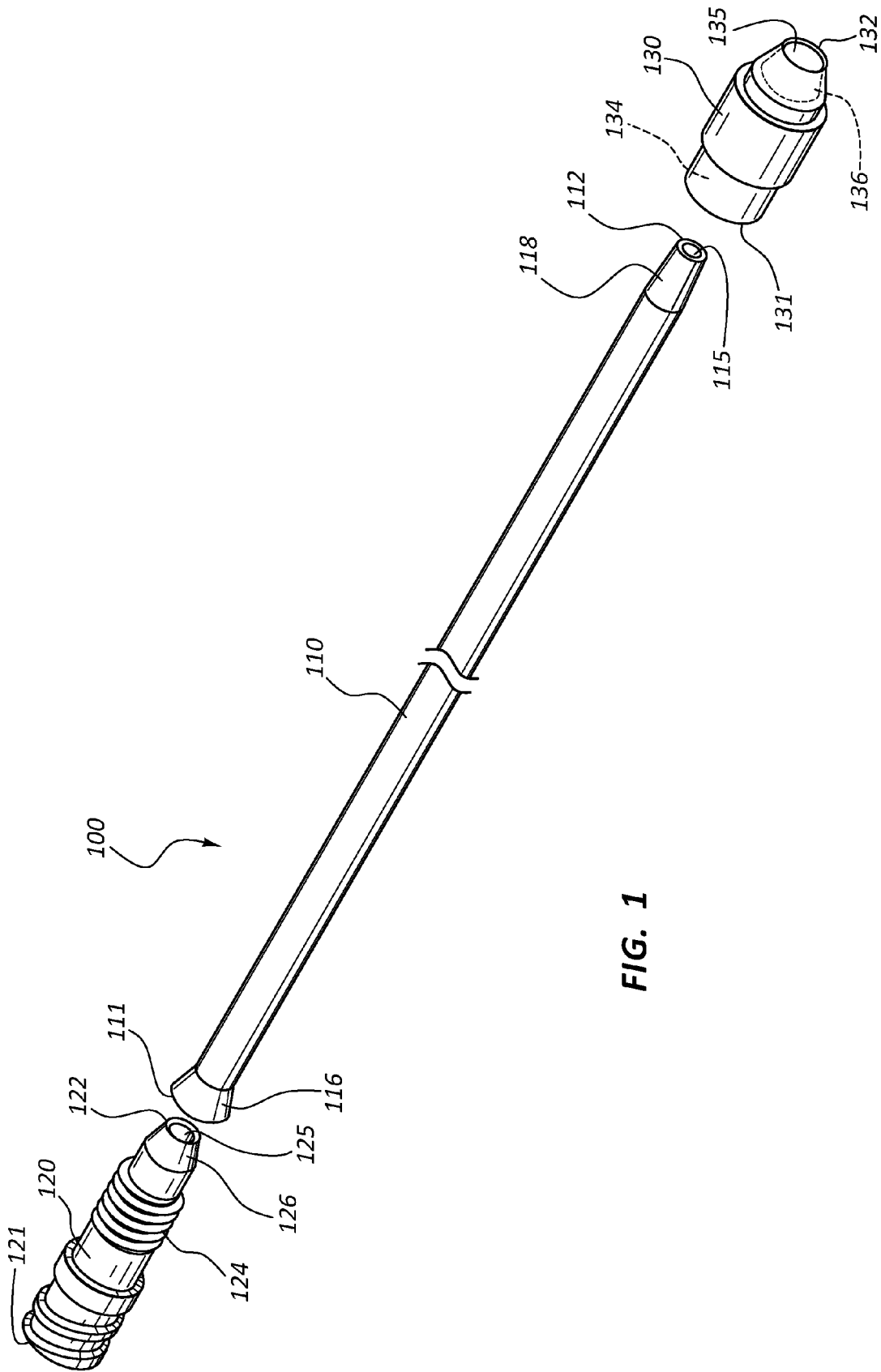
FIG. 1 is an exploded view of a catheter assembly.

Catheters may be utilized in a wide variety of medical procedures, including minimally invasive procedures. Moreover, catheters may be configured for a variety of uses, including drainage, vascular or other access, and delivery of fluids, tools, and so forth. Catheters may be formed of different lengths, with particular sizes of catheters configured for use in connection with particular therapies or access locations. For example, a catheter used for vascular access at a treatment site near a patient's heart may necessarily be longer or shorter depending on whether the vasculature is accessed at the femoral artery or the carotid artery.

Use of an appropriate length catheter may reduce the amount of excess material outside the body that would otherwise be present in using an oversized catheter. This may facilitate access and use of the catheter. Further, shorter catheters may be easier to guide or manipulate. For example, a shorter length catheter may better transfer torque or other forces along the length of the catheter, as compared to a long catheter that may twist or deform along the length of the device.

As further detailed below, catheters within the scope of this disclosure may be configured as adjustable length, or customizable length devices. In other words, such catheters may be configured such that a user, such as a medical practitioner, can cut the device to a desired length as part of a therapy. Use of adjustable length catheters may enable hospitals to better manage stock and supplies, as it may not be necessary to keep in stock many multiples of many sizes of catheters. Further, adjustable length catheters may add flexibility because medical practitioners may customize the length, rather than needing to choose between set prefabricated lengths of catheters. Moreover, adjustable length catheters may be utilized in areas or circumstances wherein stocking large numbers of premade catheters is costly or otherwise prohibitive.

It will be readily understood by one of ordinary skill in the art having the benefit of this disclosure that the components of the embodiments, as generally described and illustrated in the figures herein, could be arranged and designed in a wide variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to a catheter or elongate tube, the distal end may generally be configured to be inserted or otherwise disposed in a patient, while the proximal end may be coupled to a hub or other component configured to facilitate use of the catheter by a practitioner.

Further, a catheter, as used herein, refers broadly to any elongate medical device having at least one lumen disposed therein. The term is not meant to require any additional component, shape, or geometry, such as a hub member or a tapered tip, for example.

FIG. 1 is an exploded view of a catheter assembly 100. In the illustrated embodiment, the catheter assembly 100 comprises an elongate tube, catheter 110, and a hub member (140 of FIG. 2) comprising a lumen portion 120 and a retaining portion 130. The catheter 110 extends between a proximal end 111 and distal end 112 with a tube lumen (catheter lumen 115) disposed within the catheter 110. The distal end 112 of the catheter 110 may also comprise a tapered tip 118. The tapered tip 118 (or any other feature disposed adjacent the distal end) may be configured to facilitate particular therapies or procedures. Additionally, the proximal end 111 may comprise a flared portion 116 that may be configured to facilitate coupling of the catheter 110 to the hub member (140 of FIG. 2).

Catheters of any length are within the scope of this disclosure. In some embodiments, catheters range, for example, from about 20 cm to about 140 cm, from about 40 cm to about 120 cm, and so on. As further described below, catheters within the scope of this disclosure may be configured as adjustable length devices, such that a user can cut the catheter to length for a particular therapy. It is within the scope of this disclosure to create catheters of any length which can be shortened along all, or a portion, of the length of the catheter to create a shorter device. In some embodiments, the catheter is shortened by severing a portion of the proximal end, thus maintaining any features (such as tapers or tips) at the distal end.

The lumen portion 120 of the hub member may extend from a proximal end 121 to a distal end 122 with a hub lumen 125 disposed within the lumen portion 120. In some embodiments, the hub lumen 125 is in fluid communication with the catheter lumen 115 when the catheter assembly 100 is in an assembled configuration. For example, in the illustrated embodiment, the lumen portion 120 comprises a chamfer 126 that is adjacent the distal end 122 of the lumen portion 120. The chamfer 126 may be configured to contact, and mate with, the flare 116 of the catheter 110 when the catheter assembly 100 is assembled.

The proximal end 121 of the lumen portion 120 may be configured with a fitting or other feature configured to mate with other devices or components. For example the lumen portion may be configured for use in connection with luer connectors, Tuohy-Borst fittings, and other fittings. Such fittings may be configured to allow a practitioner to maintain pressure within the device, or may provide a hemostasis seal when the catheter assembly 100 is partially disposed within a patient.

Accordingly, the hub lumen 125 and the catheter lumen 115 may be sealed with respect to the exterior environment adjacent the distal end 122 of the lumen portion 120 and the proximal end 111 of the catheter 110. In other words, the combination of the catheter lumen 115 and the hub lumen 125 may only be in fluid communication with an environment outside the catheter assembly 100 at the proximal end 121 of the lumen portion 120 and the distal end 112 of the catheter 110. In some such embodiments, the flare 116 and the chamfer 126 create a fluidic seal when in contact.

The retaining portion 130 may extend from a proximal end 131 to a distal end 132 with retaining portion lumen 135 disposed within the retaining portion 130. Retaining portion threads 134 may be disposed on the inside diameter of a portion of the retaining portion lumen 135. The retaining portion threads 134 may be configured to mate with lumen portion threads 124 disposed on the outside diameter of the lumen portion 120. Additionally, the retaining portion 130 may comprise an angled surface 136 disposed inside the retaining portion lumen 135 adjacent the distal end 132 of the retaining portion 130. The angled surface 136 may be configured to mate with the chamfer 126 and the flare 116 when the catheter assembly 100 is in an assembled configuration. In other embodiments, other shapes or geometries are utilized at the junction of these components. Similarly, in some embodiments, other coupling mechanisms, for example, snaps, interference fits, pins, and so forth, alternatively or additionally are used in connection with the threads 124, 134.

The catheter assembly 100 may be configured such that a user, for example a medical practitioner, may slide the chamfer 126 into the flare 116 such that these elements are in contact along a longitudinal portion of each. The retaining portion 130 may then be slid up the catheter 110 and rotated such that the retaining portion threads 134 and the lumen portion threads 124 cooperatively engage. These mating threads 124, 134 may force the retaining portion 130 in a proximal direction with respect to the lumen portion 120 and the catheter 110, eventually compressing the flare 116 between the chamfer 126 and the angled surface 136. This engagement of the flare 116 by the chamfer 126 and the angled surface 136 may effectively seal the chamfer 126 and the flare 116.

Figure 2:
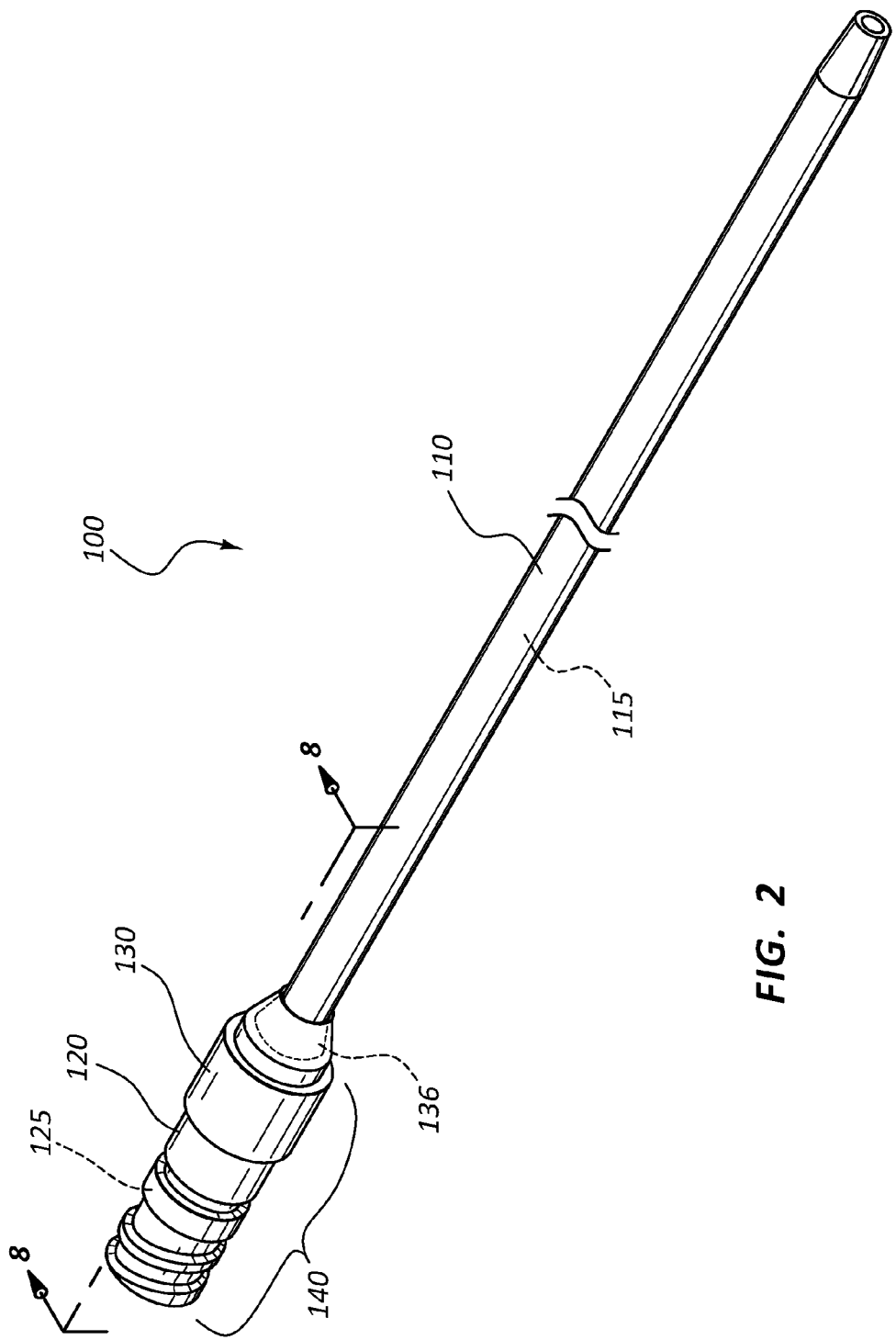
FIG. 2 is an assembled view of the catheter assembly of FIG. 1.

FIG. 2 is an assembled view of the catheter assembly 100 of FIG. 1. In this view, the lumen portion 120 and the retaining portion 130 are cooperatively engaged with the catheter 110 at the flare (116 of FIG. 1). Thus, the hub member 140 is coupled to the catheter 110. The angled surface 136, in connection with the flare (116 of FIG. 1) and the chamfer (126 of FIG. 1) provide a seal between the hub lumen 125 and the catheter lumen 115.

Referring to both FIGS. 1 and 2, in some embodiments, a catheter assembly, such as assembly 100, is configured such that a user, for example a medical practitioner, severs the catheter 110 and couples the hub 140 to the catheter 110 adjacent the point the catheter 110 was severed. As further detailed below, the user may create a new flare, analogous to flare 116, at the point of severing, or the assembly may be configured to be coupled without a flare. For example, in some embodiments, the catheter 110 comprises a slight taper along the entire length, or a portion of the length, of the catheter 110. The slight taper may taper from the proximal end 111 to the distal end 112 of the catheter 110. Such a taper may be configured to facilitate coupling of the catheter 110 to the hub 140 without flaring the catheter 110 at the point of severing.

In some embodiments, the catheter assembly 100 is configured such that a user can adjust the length of the catheter assembly 100 (for example by severing the catheter 110 and coupling the hub 140 prior to performing a therapy). Alternatively, the catheter assembly 100 may be configured to be so adjustable during a portion of a therapy. In some embodiments, the catheter assembly 100 is configured such that the catheter 110 can be shortened, and the hub 140 attached and reattached multiple times.

Figure 3A:
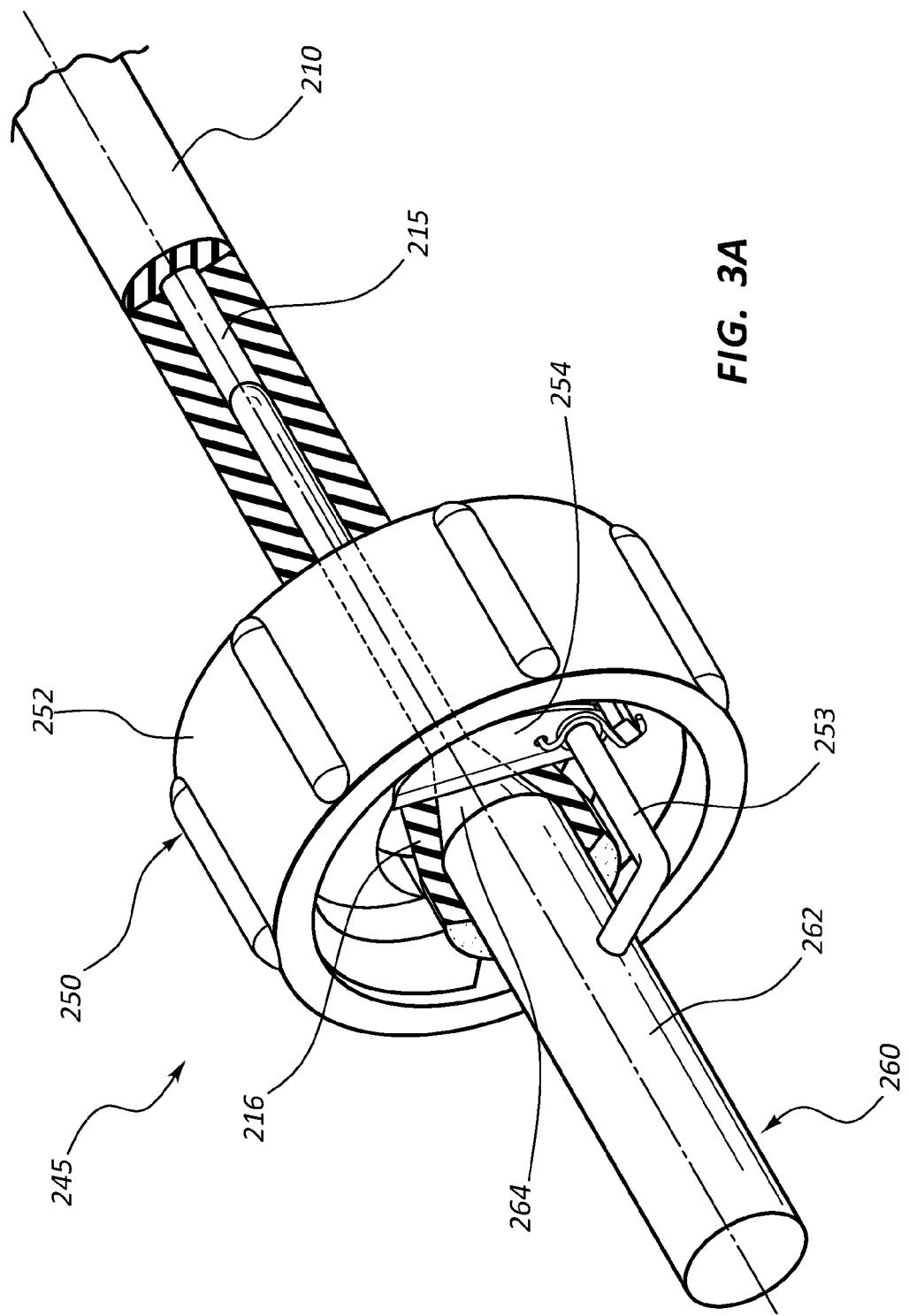
FIG. 3A is a partial view of a catheter and a cutting and flaring tool in a first position.

In some embodiments, a catheter assembly, such as assembly 100, is used in connection with a device or tool configured to cut and/or flare the catheter 110. For example, FIG. 3A is a partial view of a catheter 210 and a cutting and flaring tool 245 in a first position. The embodiment of FIG. 3A may include components that resemble components of FIGS. 1-2 in some respects. For example, the embodiment of FIG. 3A includes a catheter 210 that may resemble the catheter 110 of FIGS. 1-2. It will be appreciated that all the illustrated embodiments have analogous features. Accordingly, like features are designated with like reference numerals, with the leading digits incremented to "2." (For instance, the catheter is designated "110" in FIGS. 1-2 and an analogous catheter is designated as "210" in FIG. 3A.) Relevant disclosure set forth above regarding similarly identified features thus may not be repeated hereafter. Moreover, specific features of the catheter assembly and related components shown in FIG. 3A may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the catheter assembly and related components of FIG. 3A. Any suitable combination of the features, and variations of the same, described with respect to the catheter assembly and components illustrated in FIGS. 1-2, can be employed with the catheter assembly and components of FIG. 3A, and vice versa. This pattern of disclosure applies equally to further embodiments depicted in subsequent figures and described hereafter.

In the embodiment of FIG. 3A, the catheter 210 is disposed partially within a cutting portion 250 of the tool 245. A flaring portion 260 of the tool 245 is disposed within a catheter lumen 215 of the catheter 210. The cutting portion 250 may comprise a body member 252 that may be coupled to a cutting component, such as blade 254. The blade may be configured to sever a portion of the catheter 210.

In the illustrated embodiment, the flaring portion 260 comprises a body member 262 that is coupled to the cutting portion 250 by a coupling arm 253. The flaring portion body member 262 may further comprise an angled portion 264. The angled portion 264 may be configured to expand or otherwise deform a portion of the catheter 210 when the flaring portion 260 is disposed therein. For example, in the illustrated embodiment the angled portion 264 tapers in the proximal direction to the body member 262, which may have a larger outside diameter than the diameter of the catheter lumen 215. In some embodiments, the flaring portion 260 is simply forced into the catheter lumen 215 to flare the catheter 210. Additionally, in some instances rotation of the flaring portion 260 with respect to the catheter 210 facilitates insertion of the flaring portion 260. Additionally, in some embodiments, the flaring portion 260 is also heated prior to inserting the flaring portion 260 into the catheter 210.

Thus, use of a flaring portion, such as portion 260, may be configured to create a flare 216 on a catheter 210. Additionally, in the illustrated embodiment, because the flaring portion 260 and the cutting portion 250 are coupled, use of the tool 245 simultaneously severs the catheter 210 and flares an end of the catheter 210 adjacent the severed portion. In some embodiments, a user flushes the catheter lumen 215 after severing the catheter 210 to remove any debris. The user may flush the catheter lumen 215 by introducing a fluid through the catheter lumen 215, either in a proximal to distal direction or a distal to proximal direction. In some embodiments, a separate flushing lumen, or flushing port, is used.

Figure 3B:
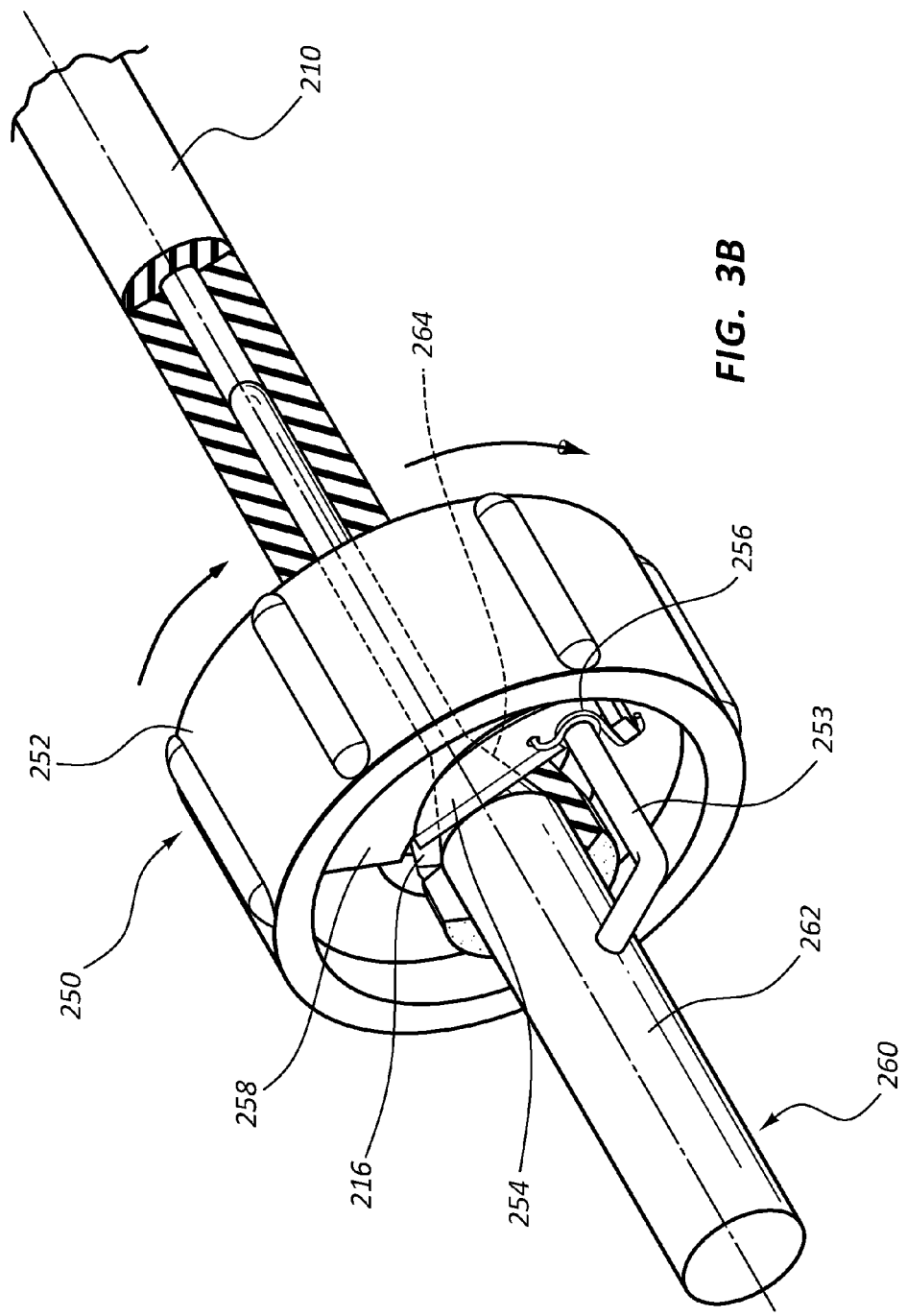
FIG. 3B is a partial view of the catheter and cutting and flaring tool of FIG. 3A in a second position.

FIG. 3B is a partial view of the catheter 210 and the cutting and flaring tool 245 of FIG. 3A in a second position. The cutting and flaring tool 245 may be configured such that rotation of the cutting portion 250 with respect to the catheter 210 severs the catheter 210. In the embodiment of FIG. 3B an engagement surface 258 interacts with the blade 254, forcing the blade 254 through a portion of the catheter 210. As indicated by the arrows in FIG. 3B, rotating the cutting portion 250 around the catheter 210 may cause the blade 254 to circumscribe the catheter 210, thereby severing the catheter 210. A biasing member, such as spring 256, may be configured to bias the blade 254 radially outward with respect to the catheter 210. Interaction of the engagement surface 258 and the blade 254 may be configured to overcome the spring 256, forcing the blade 254 into contact with the catheter 210. In some embodiments, rotation of the body member 252 of the cutting portion 250 simultaneously rotates the body member 262 of the flaring portion 260. For example, the coupling arm 253 is configured to transfer rotational displacement from the cutting portion 250 to the flaring portion 260. In other embodiments, these components are configured to rotate independently. In some such embodiments, the flaring portion 260 is configured to flare the catheter 210 only through interaction of the angled portion 264 and the catheter 210 with no rotation.

Figure 4A:
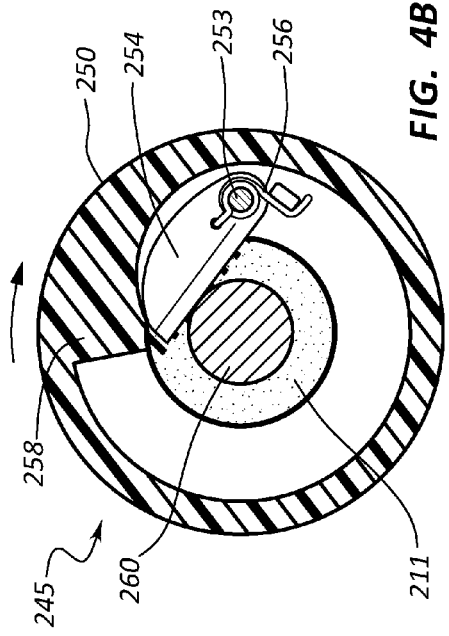
FIG. 4A is a cross-sectional view of the catheter and cutting and flaring tool of FIG. 3A in a first configuration.
Figure 4B:
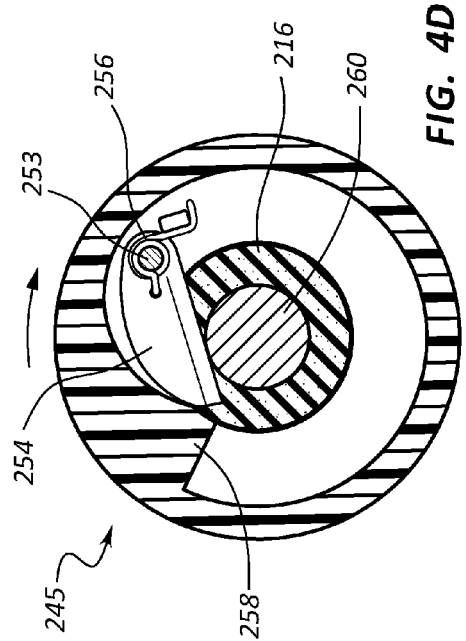
FIG. 4B is a cross-sectional view of the catheter and cutting and flaring tool of FIG. 4A in a second configuration.
Figure 4C:
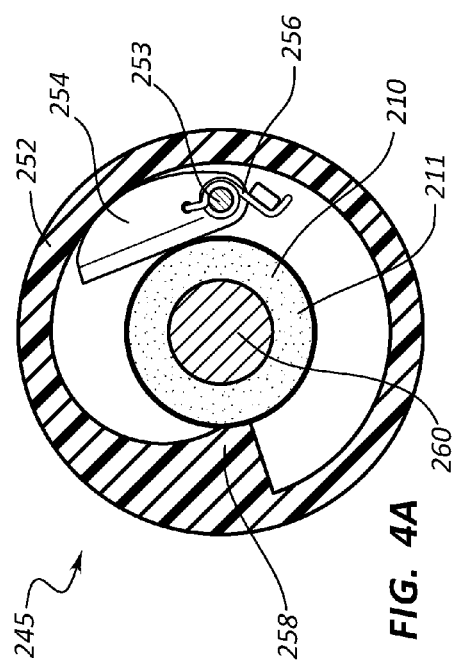
FIG. 4C is a cross-sectional view of the catheter and cutting and flaring tool of FIG. 4A in a third configuration.
Figure 4D:
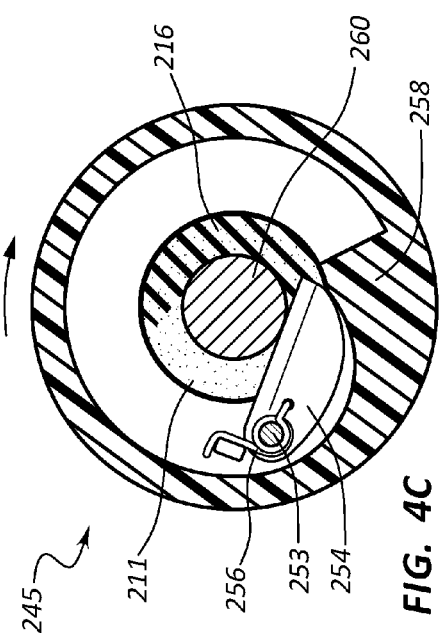
FIG. 4D is a cross-sectional view of the catheter and cutting and flaring tool of FIG. 4A in a fourth configuration.
Figure 5A:
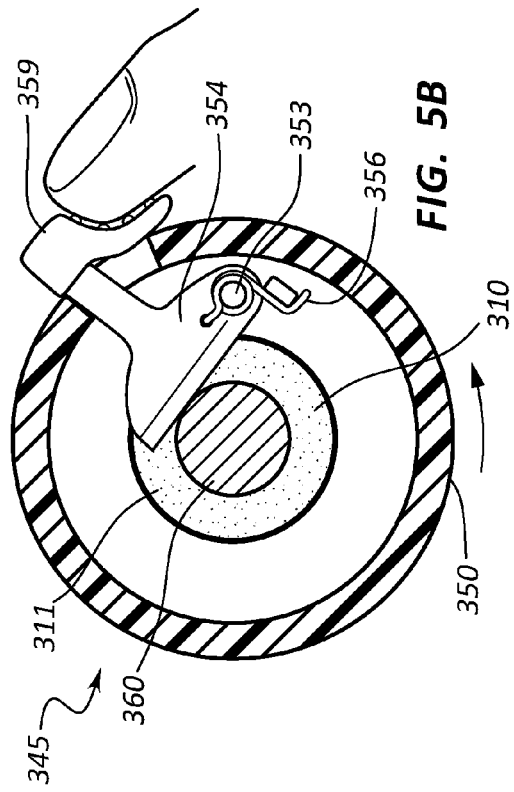
FIG. 5A is a cross-sectional view of another embodiment of a catheter and cutting and flaring tool in a first configuration.
Figure 5B:
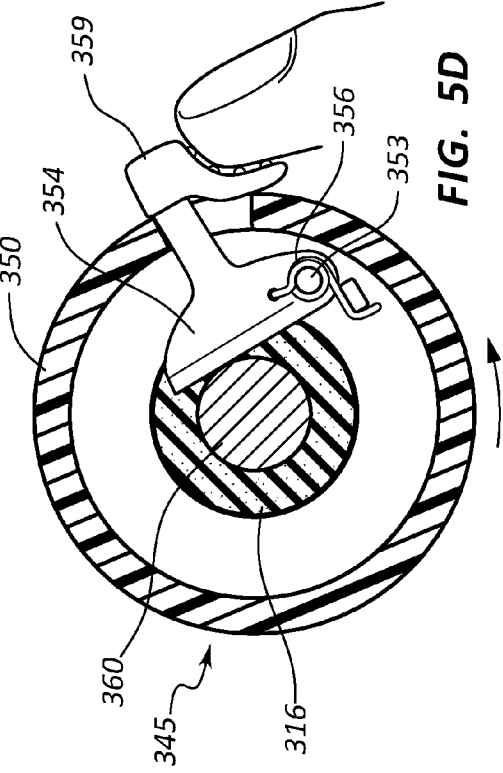
FIG. 5B is a cross-sectional view of the catheter and cutting and flaring tool of FIG. 5A in a second configuration.
Figure 5C:
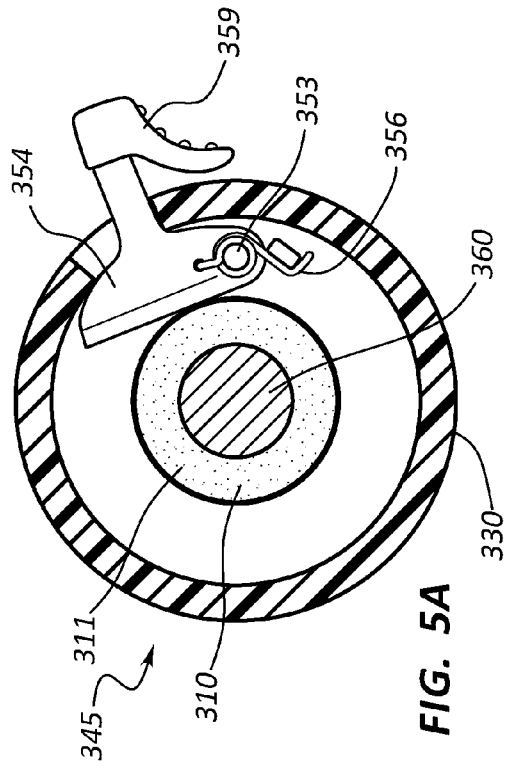
FIG. 5C is a cross-sectional view of the catheter and cutting and flaring tool of FIG. 5A in a third configuration.
Figure 5D:
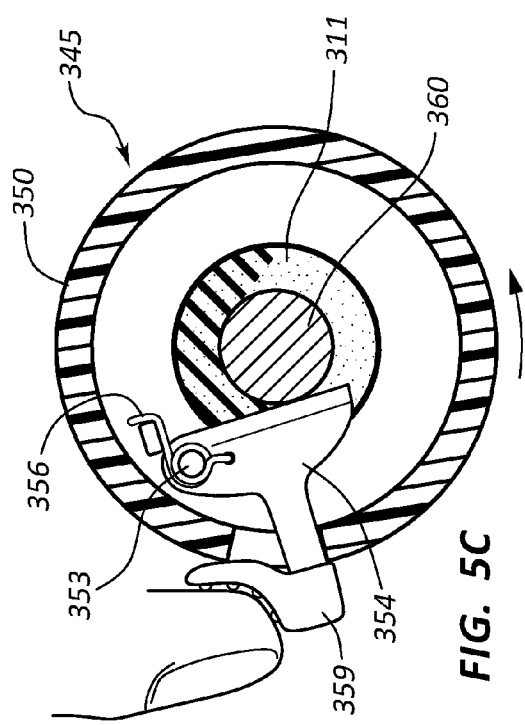
FIG. 5D is a cross-sectional view of the catheter and cutting and flaring tool of FIG. 5A in a fourth configuration.

FIGS. 4A-4D are cross-sectional views of the catheter 210 and the cutting and flaring tool 245 of FIG. 3A in various configurations. FIG. 4A is a cross-sectional view of the catheter 210 and cutting and flaring tool 245 in a first configuration wherein the blade 254 is disposed radially outward from the catheter 210. In the configurations of FIGS. 4B-4D the interaction of the engagement surface 258 and the blade 254 has forced the blade 254 into contact with the catheter 210. Each of these three views illustrates various rotational positions of the blade 254 with respect to the catheter 210.

Referring to FIGS. 4A-4D collectively, an exemplary mode of operation of the cutting and flaring tool 245 is illustrated. Specifically, in FIG. 4A the spring 256 acts to bias the blade 254 radially outward. Rotation of the body member 252 causes the engagement surface 258 to contact the blade 254, overcoming the spring 256 and forcing the blade 254 through a portion of the catheter 210. In the illustrated embodiment the blade 254 is forced completely through a wall of the catheter 210 such that the blade 254 contacts the outer diameter of the flaring portion 260. Thus, as shown in FIGS. 4B-4D, completely rotating the cutting portion 250 about the catheter 210 may cause the blade 254 to circumscribe the catheter 210 and fully sever the catheter 210. In the illustration of FIGS. 4A-4D the visible portion of the catheter 210 is designated as the proximal end 211 of the catheter 210 for the un-severed portions. For the portions of the catheter 210 cut by the blade 254 (indicated by cross-hatching) the illustrated portion of the catheter 210 is designated as the flare 216 of the catheter 210. This depiction illustrates how rotation of the cutting and flaring tool 245 may both sever and flare the catheter 210. Additionally, in the illustrated embodiment the blade 254 is configured to pivot about the coupling arm 253.

In other embodiments, actuation components or mechanisms other than an engagement surface, such as surface 258, may be utilized to actuate the blade 254. For example, FIGS. 5A-5D illustrate an analogous cutting and flaring tool 345. As with the prior embodiment, rotation of the cutting portion 350 causes the blade 354 to circumscribe, and therefore sever the catheter 310. Similar to FIGS. 4A-4D, FIGS. 5A-5D illustrate the relative positions of a catheter 310, a flaring portion 360, a cutting portion 350, a blade 354, and an engagement arm 353. A spring 356 is also shown in this embodiment. In the embodiment of FIGS. 5A-5D, an engagement trigger 359 is configured to allow a user to force the blade into contact with the catheter 310.

In the embodiment of FIGS. 5A-5D, as indicated by the arrows, the cutting portion 350 is rotated such that the forward edge (or the edge furthest from the pivot point at the engagement arm 353) of the blade 354 is configured to cut the catheter 310. In the embodiment of FIGS. 4A-4D, however, the cutting portion 250 was rotated in the opposite direction such that the portion of the blade 254 nearer the engagement arm 253 was configured to cut the catheter 210. It is within the scope of this disclosure to rotate either embodiment, or any analogous embodiments, in any direction. As with the prior embodiment in FIGS. 5A-5D the non-severed portion of the catheter 310 is designated as the proximal end 311 while the severed portion is designated as the flare 316. It will be appreciated by one of skill in the art having the benefit of this disclosure that once the catheter 210, 310 is severed the severed end becomes the proximal end of the catheter 210, 310. The convention of FIGS. 4A-5D is simply to illustrate the components during the process of severing the catheter 210, 310.

Figure 6A:
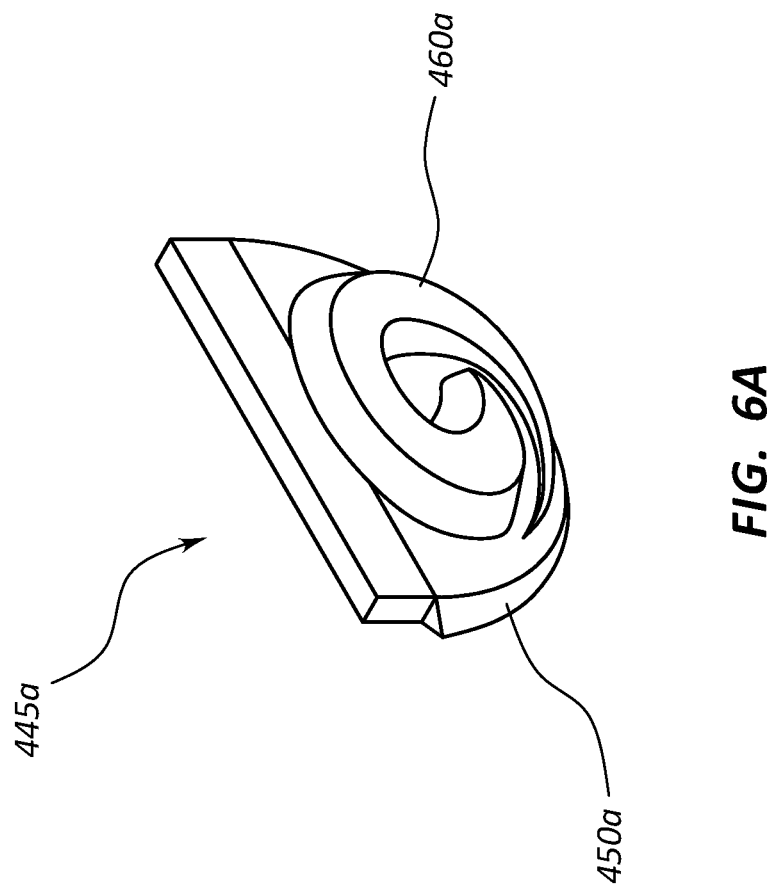
FIG. 6A is a perspective view of a portion of another embodiment of a cutting and flaring tool.

FIG. 6A is a perspective view of a portion of another embodiment of a cutting and flaring tool 445a. The cutting and flaring tool 445a comprises a cutting portion 450a and a flaring portion 460a. The cutting portion 450a may comprise a blade configured to sever a catheter. The flaring portion 460a may be coupled to a surface of the blade. In some embodiments, the blade of cutting portion 450a is used in connection with tools such as those shown in FIGS. 4A-5D. Specifically, a blade such as that of cutting portion 450a may be used in the place of blades 254 and 354 of those embodiments. The flaring portion 460a may be disposed to flare the severed end of the 410a catheter as the cutting portion 450a is rotated with respect to the catheter 410a. Thus, the flaring portion 460a, which may simply comprise an angled surface coupled to a blade, may be used in place of a flaring portion 260, 360 such as those shown in FIGS. 4A-5D.

Figure 6B:
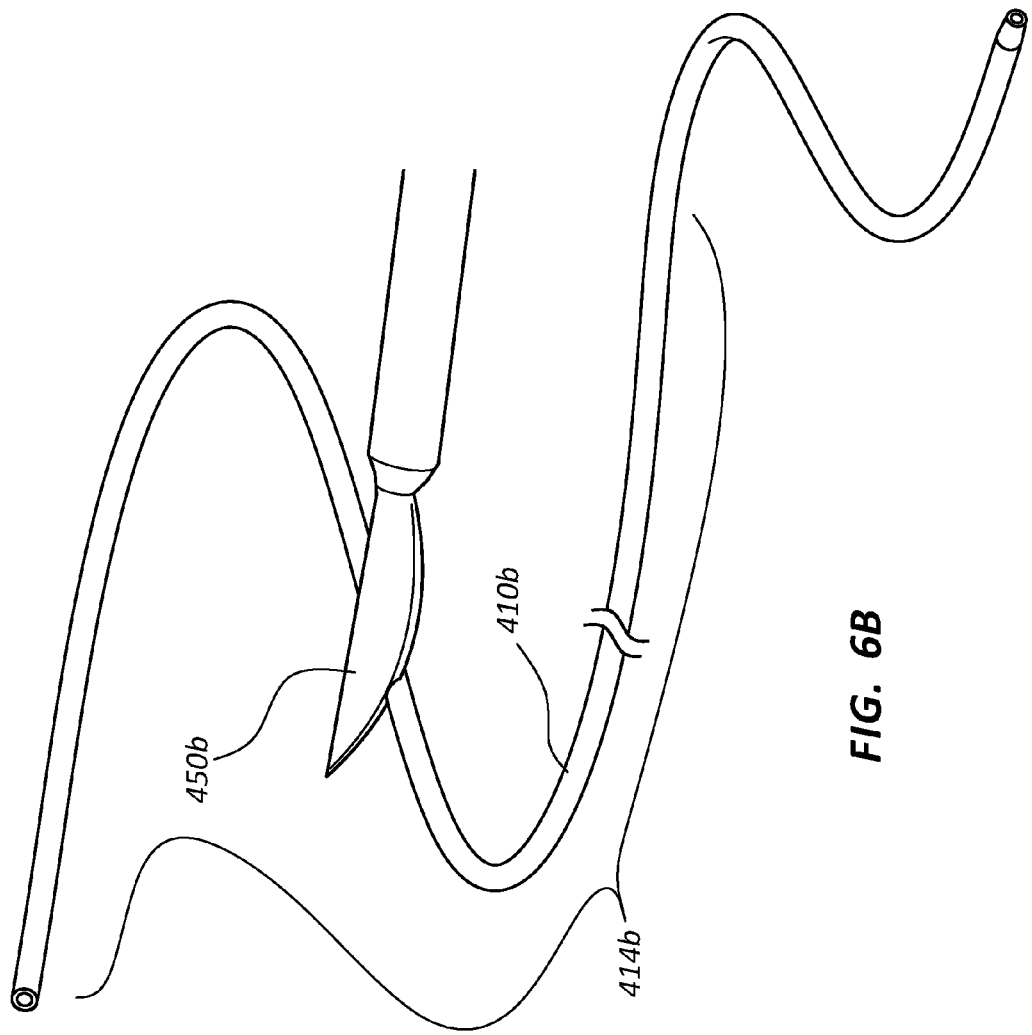
FIG. 6B is a perspective view of a catheter and an embodiment of a cutting tool.

In other embodiments, the cutting and flaring tools may be completely separate components. For example, FIG. 6B is a perspective view of a catheter 410b and an embodiment of an independent cutting tool 450b. As indicated in FIG. 6B the cutting tool 450b may simply comprise a blade or a knife.

In some embodiments, the catheter 410b comprises a segment configured to be severable. For instance, in some embodiments, a catheter 410b comprises a tapered segment 414b configured such that severing the catheter 410b at any point along the tapered segment 414b will result in a severed end with a sufficient angle or taper to mate with a hub as further described below. Thus, in some embodiments, a catheter 410b is configured such that the catheter 410b is severable and coupleable to a hub without the use of a flaring tool. In some embodiments, the tapered segment 414b is denoted by color coding or other visual indicia.

FIGS. 7A-7C are perspective views of a catheter 510 and an independent flaring tool 560 in three relative configurations. The catheter 510 may comprise a catheter lumen 515 disposed therein. Additionally, the catheter 510 may have a proximal end 511 that may or may not be created by first severing a portion of the catheter 510. The flaring tool 560 may comprise a body member 562 and an angled portion 564. The two components may be configured such that insertion of the flaring tool 560 into the catheter lumen 515 adjacent the proximal end 511 creates a flare 516 on the catheter 510. In some embodiments, the flaring tool 560 is heated. In other embodiments, the flaring tool 560 additionally or alternatively is rotated with respect to the catheter 510. Moreover, the flaring tool 560 may comprise particular features or geometries configured to interact with a particular type of catheter 510, such as a catheter that includes reinforcing fibers or other components.

In some embodiments, the angled portion 564 comprises an evenly tapered surface. In other embodiments, steps, ridges, threads, barbs, or other features are utilized in place of or in connection with the angled portion 564. Such features may be part of an independent flaring tool as shown in FIGS. 7A and 7B, or such features may be incorporated in any of the embodiments disclosed herein.

FIGS. 7A-7C, collectively, illustrate potential steps of an exemplary flaring process. FIG. 7A illustrates the catheter 510 and the flaring tool 560 prior to flaring, FIG. 7B illustrates the flaring tool 560 disposed within the catheter lumen 515, and FIG. 7C illustrates the catheter 510 and the flare 516.

As described above, the proximal end of a catheter, whether or not severed and/or flared, may be configured to be coupled to a hub. FIG. 8 is a cross-sectional view of an embodiment of a catheter assembly 600. The embodiment of FIG. 8 is analogous to the embodiment previously described in FIGS. 1 and 2. Plane 8-8 in FIG. 2 illustrates the cross-sectional plane of FIG. 8 as it would be taken through the analogous embodiment of FIG. 2. Notwithstanding the similarities in the embodiments, the embodiment of FIG. 8 is denoted with unique reference numerals. The catheter assembly of FIG. 8 comprises a catheter 610 having a proximal end 611, a flare 616, and a catheter lumen 615. The flare 616 and/or proximal end 611 may or may not be formed according to the severing or flaring processes disclosed above.

The catheter 610 is coupled to a hub member 640. The hub member 640 comprises a lumen portion 620 and a retaining portion 630. Mating threads 624, 634 on the lumen portion 620 and the retaining portion 630, respectively, are configured to couple the retaining portion 630 and the lumen portion 620. The lumen portion 620 extends from a proximal end 621 to a distal end 622 with a hub lumen 625 disposed therein. A chamfer 626 adjacent the distal end 622 of the lumen portion 620 is configured to be disposed in, and mate with, the flare 616 of the catheter 610. Additionally, an angled surface 636 of the retaining portion 630 is configured to cooperatively and/or compressibly engage the flare 616 between the angled surface 636 and the chamfer 626. The retaining portion 630 may have a proximal end 631, a distal end 632, with a retaining portion lumen 635 disposed therein.

The interaction of the chamfer 626, the flare 616, and the angled surface 636 may effectively seal the catheter lumen 615 and the hub lumen 625. This seal may facilitate use of the assembly in various procedures including, for example, vascular access. In some instances, a user pressurizes the catheter lumen 615 to test the seal prior to use.

Additionally, the chamfer 626 may be configured to provide a transition between the hub lumen 625 and the catheter lumen 615. The chamfer 626 may allow the lumen portion 620 to overlap the catheter 610 in order to prevent the proximal end 611 of the catheter 610 from interfering with the advancement of instruments, such as guidewires, from the hub lumen 625 to the catheter lumen 615. In other embodiments, the chamfer 626, or an analogous element, is configured to provide a transition section but may or may not be configured to seal the hub lumen 625 and the catheter lumen 615.

Figure 9:
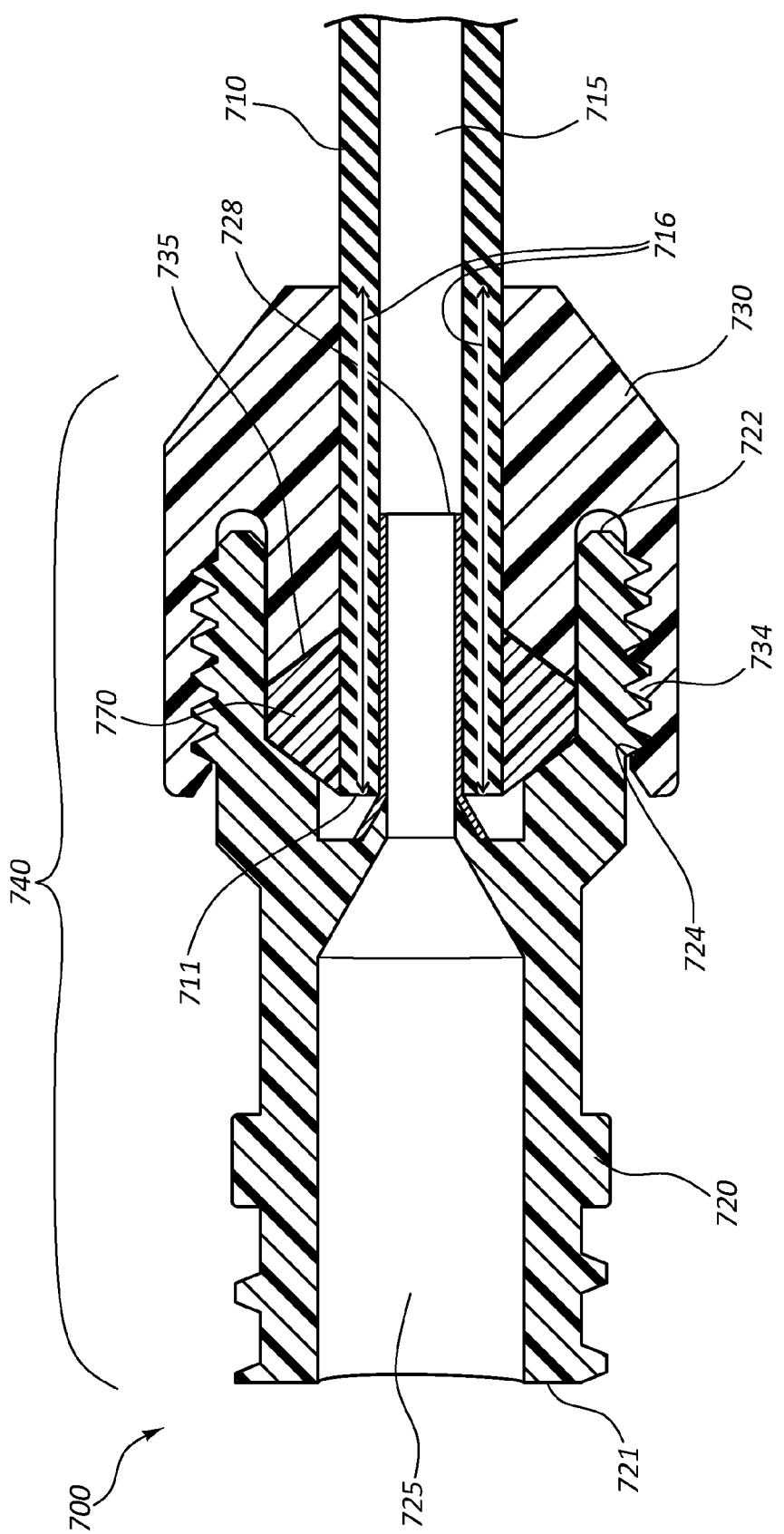
FIG. 9 is a cross-sectional view of another embodiment of a catheter assembly.

FIG. 9 is a cross-sectional view of another embodiment of a catheter assembly 700. The assembly 700 comprises a catheter 710 extending from a proximal end 711 and comprising a catheter lumen 715. The proximal end 711 of the catheter 710 may not comprise a flare (such as 616 of FIG. 8), but the catheter 710 may comprise a tapered portion 716 adjacent the proximal end 711.

The catheter assembly 700 further comprises a hub member 740. The hub member 740 may comprise a lumen portion 720 extending from a proximal end 721 to a distal end 722 with a hub lumen 725 disposed therein. Mating threads 724, 734 on the lumen portion 720 and a retaining portion, such as compression nut 730, respectively, may be configured to couple the compression nut 730 to the lumen portion 720.

In the embodiment of FIG. 9, the lumen portion 720 comprises a cannula 728 configured to overlap the catheter 710. The cannula 728 may provide a transition section and prevent tools or other devices disposed within the hub lumen 725 from catching on the proximal end 711 of the catheter 710 as the tools are advanced from the hub lumen 725 into the catheter lumen 715. The cannula 728 may comprise a thin-walled cylinder with sufficient strength to facilitate compression of a proximal portion, such as tapered portion 716 of the catheter 710 between the compression nut 730 and the cannula 728. In some embodiments, the cannula 728 may be comprised of steel. Additionally, the cannula 728 may comprise a sufficiently thin-walled material to minimize the overall diameter of the catheter assembly 700. Further, the cannula 728 may be flared in a distal to proximal direction, allowing the smaller tip to fit more easily into the proximal end 711 of the catheter 710.

In the illustrated embodiment, a compression sleeve 770 is disposed between the catheter 710 and the lumen portion 720, adjacent the proximal end 711 of the catheter 710. The compression sleeve 770 may comprise a resilient material configured to exert pressure on the catheter 710 when the compression nut 730 is advanced proximally. For example, the compression nut 730 may comprise an angled surface 735 configured to compress the compression sleeve 770 and pinch the catheter 710 between the compression sleeve 770 and the cannula 728 to secure the catheter 710 within the hub member 740. In some embodiments the compression sleeve 770 may be integral with the compression nut 730.

Catheter assemblies, such as assembly 700, comprising a cannula 728 may be used in connection with catheters 710, which comprise severable tapered segments as also described above. The cannula 728 may be configured to slide into the catheter lumen 715 when the catheter 710 is severed at any point along the tapered segment. In some embodiments, the majority of the length of the catheter 710 is so tapered.

Without further elaboration, it is believed that one skilled in the art can use the preceding description to utilize the present disclosure to its fullest extent. The examples and embodiments disclosed herein are to be construed as merely illustrative and exemplary, and not a limitation of the scope of the present disclosure in any way. It will be apparent to those having skill in the art that changes may be made to the details of the above-described embodiments without departing from the underlying principles of the disclosure herein. It is intended that the scope of the invention be defined by the claims appended hereto and their equivalents.

The invention claimed is:

1. A catheter assembly kit comprising:
   an elongate tube;
   a hub member configured to be coupled to the elongate tube by a user;
   a cutting tool configured to sever the elongate tube;
   a flare tool configured to flare an end of the elongate tube; and
   a body member that is coupled to the flare tool and the cutting tool;
   wherein rotation of the body member about the elongate tube is configured to simultaneously sever and flare the elongate tube.

2. The catheter assembly kit of claim 1, wherein the hub member comprises a lumen portion and a retaining portion, the lumen portion and the retaining portion configured to engage the elongate tube when the hub member is coupled to the elongate tube.

3. The catheter assembly kit of claim 2, wherein the hub member is configured to seal an end of the elongate tube from an external environment when the hub member is coupled to the elongate tube.

4. The catheter assembly kit of claim 3, wherein a hub lumen disposed within the lumen portion is configured to be in fluid communication with a tube lumen of the elongate tube when the hub member is coupled to the elongate tube.

5. The catheter assembly kit of claim 3, wherein mating surfaces on the lumen portion and the retaining portion are configured to compressibly engage the elongate tube.

6. The catheter assembly kit of claim 3, wherein the lumen portion comprises a transition section configured to overlap a portion of the elongate tube.

7. The catheter assembly kit of claim 6, wherein the transition section is flared.

8. The catheter assembly kit of claim 1, wherein the assembly is configured such that a user may sever the elongate tube and couple the hub member to the tube adjacent a severed end of the elongate tube.

9. The catheter assembly kit of claim 8, wherein the elongate tube comprises a tapered segment, the tapered segment configured to mate with the lumen portion of the hub if the elongate tube is severed at any point along the tapered segment.

10. The catheter assembly kit of claim 9, wherein visual indicia on the elongate tube indicate the location of the tapered segment.

11. A method of treating a patient with a catheter, comprising:
    obtaining the catheter assembly kit of claim 1;
    coupling the hub member to the elongate tube; and
    treating a patient through use of the elongate tube.

12. The method of claim 11, further comprising severing a portion of the elongate tube prior to coupling the hub member to the elongate tube.

13. The method of claim 12, further comprising determining what length of elongate tube is desirable for treatment prior to severing the portion of the elongate tube and wherein severing a portion of the elongate tube comprises severing the elongate tube at the determined length.

14. The method of claim 13, further comprising observing visual indicia on the elongate tube, the visual indicia configured to indicate a severable portion of the elongate tube, and severing the elongate tube comprises severing the elongate tube in the severable portion.

15. The method of claim 12, further comprising flaring a severed end of the elongate tube prior to coupling the hub member to the elongate tube.

16. The method of claim 12, further comprising flushing the elongate tube.

* * * * *